United States Patent [19]

Petersen et al.

[11] Patent Number: 5,507,763
[45] Date of Patent: Apr. 16, 1996

[54] SURGICAL SAW BLADE

[75] Inventors: Thomas D. Petersen, San Diego; Gregory A. Goris, Ojai, both of Calif.

[73] Assignee: Hall Surgical, Carpenteria, Calif.

[21] Appl. No.: 322,243

[22] Filed: Oct. 12, 1994

Related U.S. Application Data

[63] Continuation of Ser. No. 94,594, Jul. 19, 1993, abandoned.

[51] Int. Cl.⁶ ..................................................... A61B 17/14
[52] U.S. Cl. ................................... 606/176; 30/166.3
[58] Field of Search ........................... 606/82, 176–179; 30/166.3, 392, 393, 351; 83/835

[56] References Cited

U.S. PATENT DOCUMENTS

| | | |
|---|---|---|
| 336,697 | 2/1886 | Clemson . |
| 486,426 | 11/1892 | Brooks . |
| 563,521 | 7/1896 | Walter . |
| 1,929,838 | 10/1933 | Crane ................................ 56/326 |
| 2,958,943 | 11/1960 | Koe ..................................... 30/115 |
| 2,974,051 | 3/1961 | Moore ................................. 106/18 |
| 3,496,973 | 2/1970 | Ballard ............................... 143/133 |
| 3,615,309 | 10/1971 | Dawson .............................. 51/309 |
| 3,743,556 | 7/1973 | Breton et al. .................... 156/62.8 |
| 3,754,968 | 8/1973 | Reznik ................................ 117/46 |
| 3,905,374 | 9/1975 | Winter .............................. 30/166.3 |
| 4,252,121 | 2/1981 | Arnegger .......................... 606/178 |
| 4,379,121 | 4/1983 | McMurray et al. ............... 420/452 |
| 4,386,609 | 6/1983 | Mongeon . |
| 4,513,742 | 4/1985 | Arnegger .......................... 606/178 |
| 4,584,999 | 4/1986 | Arnegger ............................ 30/351 |
| 4,596,691 | 6/1986 | Ruppert et al. ..................... 419/3 |
| 4,617,930 | 10/1986 | Saunders .......................... 606/178 |
| 4,671,932 | 6/1987 | Lutz et al. ........................ 420/452 |
| 4,745,037 | 5/1988 | DeCristofaro et al. ........... 428/678 |
| 4,754,950 | 7/1988 | Tada et al. ........................ 251/368 |
| 4,768,504 | 9/1988 | Ender .............................. 30/166.3 |
| 4,830,934 | 5/1989 | Ferrigno et al. ................. 428/678 |
| 4,955,888 | 9/1990 | Slocum ............................. 606/176 |
| 5,002,555 | 3/1991 | Petersen .......................... 606/176 |
| 5,133,728 | 7/1992 | Petersen .......................... 606/176 |
| 5,135,533 | 8/1992 | Petersen et al. ................. 606/176 |
| 5,149,597 | 9/1992 | Holko .............................. 428/680 |
| 5,178,626 | 1/1993 | Pappas ............................. 606/178 |

FOREIGN PATENT DOCUMENTS

| | | | |
|---|---|---|---|
| 378189 | 7/1990 | European Pat. Off. | ............. 606/82 |
| 2030072 | 4/1980 | United Kingdom | ............ 606/176 |
| 9301751 | 2/1993 | WIPO | ......................... 606/176 |

Primary Examiner—Stephen C. Pellegrino
Assistant Examiner—Nancy Mulcare
Attorney, Agent, or Firm—Todd A. Dawson; Gene Warzecha

[57] ABSTRACT

An oscillating surgical blade formed such that the thickness of the blade adjacent the side edges is reduced relative to the effective thickness of the body of the blade. Therefore, when the side edges of the blade mushroom due to contact with a saw guide slot, the resultant thickness of the mushroomed edges is less than or equal to the effective thickness of the blade body.

3 Claims, 2 Drawing Sheets

SURGICAL SAW BLADE

This application is a continuation of application Ser. No. 08/094,595, filed Jul. 19, 1993, now abandoned.

FIELD OF THE INVENTION

This invention relates to surgical saw blades and has specific relevance to oscillating saw blades for use with cutting guides.

BACKGROUND OF THE INVENTION

Surgical saw blades as used in orthopaedic surgery may be generally categorized as either reciprocating or oscillating. An oscillating blade, when connected at its proximal end to a hub of a powered surgical saw, pivots about the hub such that the distal end reciprocates in an arc-like manner. An example of such an oscillating blade may be had by reference to U.S. Pat. No. 5,135,555. Often, such oscillating blades are used in conjunction with a cutting guide to provide for a precision cut. The cutting guide commonly has a head of some type with a slot therethrough having side walls. As the surgeon cuts along the slot with the oscillating blade, the sides of the blades can violently hit against the side walls of the guide causing the lateral side walls of the blades to deform or mushroom out. The mushrooming of the blades' sides can cause the blade to rub against the slot, thereby increasing friction therebetween, which in turn can cause a higher torque on the powered instrument. Increased friction can also increase the heat and debris at the resection site. Further, with excessive mushrooming the blade could jam within the cutting guide. Finally, it is known in the industry to apply a coating to the exterior of a blade to reduce galling of the blade during use. Mushroomed edges scrapping against the cutting guide can scrape off the gall-resistent coating along the edge.

While most oscillating saw blades have radiused corners along the lateral side walls, it is known to provide a fully arcuate lateral side wall on an oscillating blade.

SUMMARY OF THE INVENTION

The oscillating blade of this invention solves the problems discussed above by forming the blade such that the thickness of the blade adjacent the lateral side walls is reduced relative to the effective thickness of the body of the blade. Therefore, when the side edges of the blade mushroom, the resultant thickness of the mushroomed edges is less than or equal to the effective thickness of the blade body. In essence, the occurrence of mushrooming of the lateral side walls is planned for and compensated by the design to prevent interference between the mushroomed edges and the cutting guide.

Accordingly, it is an advantage of the invention to provide a novel oscillating surgical saw blade having a reduced thickness adjacent the lateral edges.

Another advantage of the invention is to provide for a novel oscillating saw blade having a reduced thickness adjacent its lateral side edges to control mushroom deformation during use.

Other advantages of the invention will become apparent upon a reading of the following description taken with the accompanying drawings.

DESCRIPTION OF THE PRIOR ART

Figure 1:
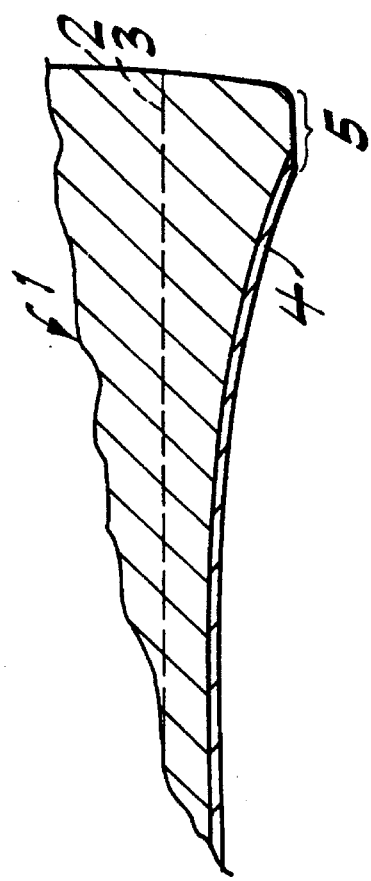
FIG. 1 is a partial cross section of a prior art blade which has experienced mushroom deformation from contact with side walls of a saw guide (not shown).
Figure 2:
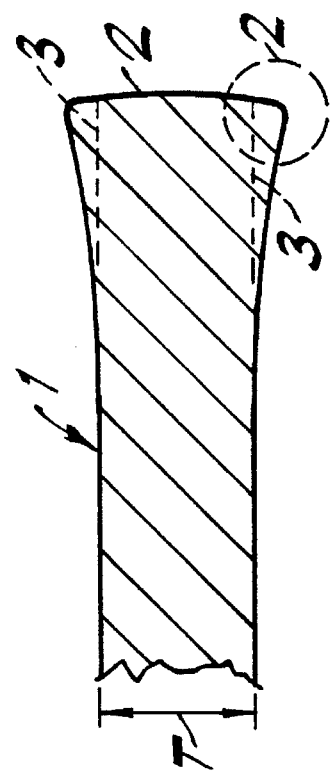
FIG. 2 is an enlarged view of the area circled in FIG. 1 illustrating the absence of gall-resistent coating at the point of the mushroomed edge.

FIGS. 1 and 2 illustrate in partial cross section a common oscillating saw blade 1 after use with a saw guide (not shown). This use is evident by the deformation of the lateral edge 2 such that the edge 2 extends above the effective thickness T of the blade body. Prior to use, the lateral side edge 2 of the blade 1 was also at thickness T as illustrated by the broken line 3 in FIG. 1. FIG. 2 is an enlargement of the circled area in FIG. 1 and illustrates the prior art coating 4 that may be applied to a saw blade to resist galling during use. A more thorough explanation of the coating and its use may be had by reference to U.S. Pat. No. 5,135,555, incorporated herein by reference. FIG. 2 illustrates that with the lateral edge 2 being greater than thickness T due to mushroom deformation, a portion 5 of the coating 4 at the apex of the deformed lateral edge has been scraped off or abraded due to contact with the guide slot of a cutting head (not shown). The lack of a gall-resistent coating at this point can contribute to the galling of the blade and the increase in friction, heat, and debris. Further, the deformation of the blade is undesirable from a mechanical point of view possibly contributing to the jamming of the blade within the slot or to inaccuracies in the cut.

DESCRIPTION OF THE PREFERRED EMBODIMENT

The preferred embodiment herein described is not intended to be exhaustive or to limit the invention to the precise form disclosed. Rather, it is chosen and described to best explain the invention so that others skilled in the art might utilize its teachings.

Figure 3:
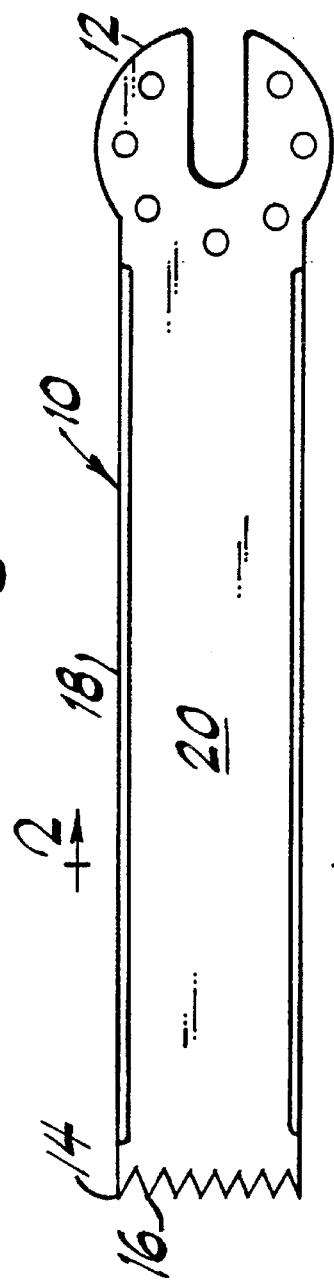
FIG. 3 is an elevational view of an oscillating saw blade of the invention.
Figure 5:
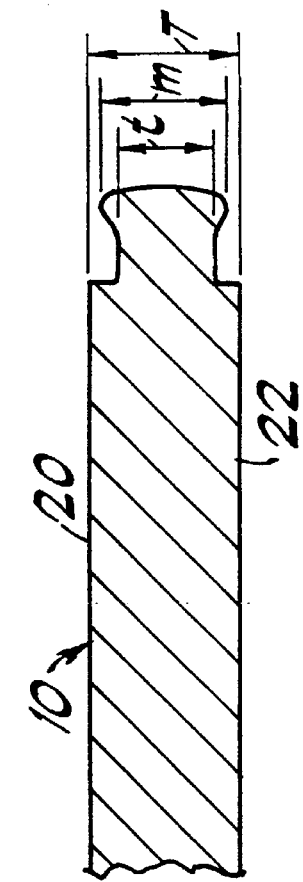
FIG. 5 is a partial cross sectional view of the blade of FIG. 2 experiencing mushroom deformation caused by use with a saw guide.
Figure 4:
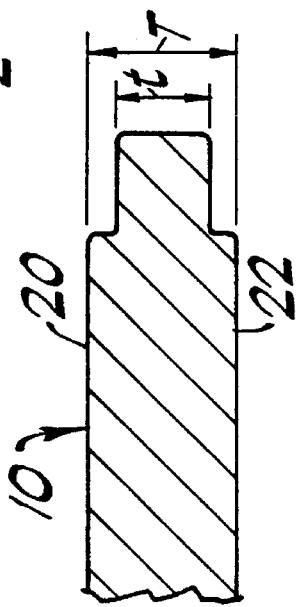
FIG. 4 is a partial cross sectional view of the blade of FIG. 1.

As illustrated in the FIGS. 3–5, blade 10 has a hub end 12 configured for connection to the collet of a power instrument (not shown) and a toothed end 14 having a plurality of cutting teeth 16 formed thereon. Blade 10 further includes lateral side walls 18 extending from hub end 12 to toothed end 14. An upper surface 20 and a lower surface 22 of the blade define an effective thickness T. The term effective thickness is used to encompass a blade having solid upper and lower surfaces as shown or a blade having one or more ribs or otherwise areas of reduced cross section wherein the uppermost and lowermost portions of the ribs define the upper and lower surfaces of the blade. Each lateral side wall is formed having a reduced thickness t relative to thickness T as is illustrated in FIG. 4. Thickness t along the lateral side wall extends inwardly from the side wall a distance 1.

When the blade is connected to a powered instrument (not shown) and used in conjunction with a saw guide having a saw blade guide slot with end walls (also not shown), the lateral side walls will contact the slot end walls and be deformed in the mushroom-like shape illustrated in FIG. 5. However, since the lateral side walls are formed having a thickness t which is less than thickness T, the extent of the mushrooming is controlled such that the thickness m of the mushroomed lateral side wall is less than or equal to thickness T of the blade. Therefore, the lateral side wall, when deformed during use, will not form an interference with the cutting guide slot. Further, with the mushroomed edge being less than or equal to thickness T, any lubricous or gall-resistent coating on the blade will not be scraped off by the slot.

It should be understood that the invention is not to be limited to the precise forms disclosed but may be modified within the keeping of the appended claims.

We claim:

1. A saw blade for use in surgery, the blade having a first end configured for connection to a powered surgical instrument and a second end having a plurality of teeth formed thereon, the blade having a length and a width wherein the length is greater than the width, a pair of side walls which extend between the first and second end along the length of the saw blade, and upper and lower blade surfaces each extending between the side walls;

the blade having a thickness in cross section defined by the upper and lower surfaces, the thickness of a portion of the blade adjacent each of the side walls being a thickness t, the thickness of a portion of the blade spaced from the side walls being a thickness T, wherein thickness T is greater than thickness t, and wherein the portions of the blade spaced from the side walls abut each of the portions of the blade adjacent the side walls and forms a shoulder at each abutment which extends substantially the length of the blade.

2. An oscillating saw blade for use in surgery and configured to be guided by a slot in a cutting guide, said saw blade being generally elongated, having a width and length upper and lower surfaces, a hub end configured for connection to an oscillating powered surgical instrument, a toothed end, and a pair of generally parallel side wails extending along the length of the blade from the hub end to the toothed end, said blade having a thickness in cross section defined by the upper and lower surfaces, the thickness of a portion of the blade adjacent each of the side walls being a thickness t, the thickness of a portion of the blade spaced from the side walls being a thickness T, wherein thickness T is greater than thickness t, and wherein the portions of the blade spaced from the side walls abut each of the portions of the blade adjacent the side walls and forms a shoulder at each abutment which extends substantially along the length of the blade.

3. A saw blade for use in a medical procedure, the saw blade having a first end configured for connection to surgical tool and a second toothed end, upper and lower surfaces extending from the tool engaging end to the toothed end of the blade, a pair of side walls which extend between the first and second end, the extension defining the length of the blade, said upper and lower blade surfaces each extending between the side walls along the blade's length;

said blade having a thickness in cross section defined by the upper and lower surfaces, the thickness of a portion of the blade adjacent each of the side walls being a thickness t, the thickness of a portions of the blade spaced from the side walls being a thickness T, wherein thickness T is greater than thickness t, and wherein the portions of the blade spaced from the side walls abuts each of the portions of the blade adjacent the side walls and forms a shoulder at each abutment which extends the length of the abutment which is a substantial portion of the length of the blade.

* * * * *